(12) United States Patent
Gao

(10) Patent No.: US 8,323,573 B2
(45) Date of Patent: Dec. 4, 2012

(54) MICROFLUIDIC CARTRIDGE WITH SOLUTION RESERVOIR-PUMP CHAMBER

(75) Inventor: Yunhua Gao, Beijing (CN)

(73) Assignee: Xizeng Shi, Beijing (CN)

(*) Notice: Subject to any disclaimer, the term of this patent is extended or adjusted under 35 U.S.C. 154(b) by 98 days.

(21) Appl. No.: 12/747,889

(22) PCT Filed: Dec. 12, 2008

(86) PCT No.: PCT/CN2008/073472
§ 371 (c)(1),
(2), (4) Date: Oct. 7, 2010

(87) PCT Pub. No.: WO2009/076904
PCT Pub. Date: Jun. 25, 2009

(65) Prior Publication Data
US 2011/0020182 A1      Jan. 27, 2011

(30) Foreign Application Priority Data
Dec. 14, 2007   (CN) .......................... 2007 1 0198600

(51) Int. Cl.
*G01N 27/00*   (2006.01)
(52) U.S. Cl. ...................... 422/82.02; 422/129; 422/417; 422/503; 422/504; 422/537; 422/542; 251/120; 137/511; 137/42; 137/798; 137/829; 137/832
(58) Field of Classification Search ............... 422/82.02, 422/129, 417, 503, 504, 537, 543; 251/120; 137/511, 42, 798, 829, 832
See application file for complete search history.

(56) References Cited

U.S. PATENT DOCUMENTS 5,831,784 A * 11/1998 Barnett et al. .................. 360/67
(Continued)

FOREIGN PATENT DOCUMENTS

| CN | 1534290 A | 10/2004 |
|---|---|---|
| CN | 1598579 A | 3/2005 |
| WO | WO 2005/116661 A1 | 12/2005 |
| WO | WO 2007/125468 A2 | 11/2007 |

OTHER PUBLICATIONS

PCT International Search Report for PCT Counterpart Application No. PCT/CN2008/073472 containing Communication relating to the Results of the Partial International Search Report, 6 pgs., (Mar. 12, 2009).

*Primary Examiner* — In Suk Bullock
*Assistant Examiner* — Timothy G Kingan
(74) *Attorney, Agent, or Firm* — Blakely, Sokoloff, Taylor & Zafman LLP

(57) ABSTRACT

A microfluidic cartridge with solution reservoir-pump chamber is disclosed. The microfluidic cartridge comprises a channel-chamber layer, a sealing layer, a printed circuit board bound with magnetoresistive biochip. The channel-chamber layer includes at least a waste reservoir, a reaction-detection chamber, a solution reservoir-pump chamber and a plurality of micro-channels. Said solution reservoir-pump chamber realizes both functions of solution reservoir and pump chamber in a single structure. Said sealing layer is sealed with said channel-chamber layer to form an integrated microfluidic system with at least a waste reservoir, a reaction-detection chamber, a solution inlet, a solution reservoir-pump chamber and a micro-channel. Said solution reservoir-pump chamber in the present invention consists of elastic objects inside for sealing and pumping. Under pressure, said elastic object propels solution in the reservoir into said reaction-detection chamber via channels of said plurality of micro-channels.

7 Claims, 6 Drawing Sheets

U.S. PATENT DOCUMENTS

| | | | |
|---|---|---|---|
| 6,229,301 B1 * | 5/2001 | Bolli et al. | 324/207.21 |
| 6,284,113 B1 * | 9/2001 | Bjornson et al. | 204/453 |
| 6,581,899 B2 * | 6/2003 | Williams | 251/7 |
| 6,929,239 B1 * | 8/2005 | Colin et al. | 251/115 |
| 2003/0197139 A1 * | 10/2003 | Williams | 251/7 |
| 2005/0130292 A1 * | 6/2005 | Ahn et al. | 435/287.1 |
| 2007/0166196 A1 * | 7/2007 | Bardell et al. | 422/68.1 |
| 2007/0264159 A1 * | 11/2007 | Graham et al. | 422/99 |
| 2009/0074626 A1 * | 3/2009 | Kadel et al. | 422/102 |

\* cited by examiner

MICROFLUIDIC CARTRIDGE WITH SOLUTION RESERVOIR-PUMP CHAMBER

CROSS-REFERENCE TO RELATED APPLICATION

This patent application is a U.S. National Phase application under 35 U.S.C. §371 of International Application No. PCT/CN2008/073472, filed on Dec. 12, 2008, entitled A MICROFLUID SAMPLE BOAT WITH SOLUTION STORAGE CHAMBER AND PUMP, which claims priority to Chinese patent application no. 200710198600.3, filed on Dec. 14, 2007.

FIELD OF THE INVENTION

The invention relates to microfluidic biochips for testing chemical and biological samples, particularly to microfluidic cartridge with magnetic sensor biochips in the microfluidic channels of said cartridge wherein chemical and biological samples are injected and the bio molecules in said samples are screened and detected.

BACKGROUND OF THE INVENTION

The development of microfluidic technology, which handles and analyzes micro-liter or nanoliter volume of solution, has enabled the transition of the laboratory-on-a-chip (LOC) or microfluidic technology from research labs to industry. In the fields of chemistry and biology, microfluidic systems are increasingly used in applications such as transmission of trace fluid, micro synthesis, sample separation, composition analysis and chemical reaction.

Most microfluidic chips disclosed so far are electrophoresis chips, wherein molecules in solutions are driven by electrophoresis and/or electro-osmosis to the reaction surface. Electrophoresis chips can handle trace solution, but the repeatability and controllability of such a process are poor. On the other hand, fluid handling with a syringe is simple, but a relatively large volume of solution and reagent is usually consumed for such a procedure and hence waste of solution occurs frequently. Therefore, many researchers are developing various technologies and devices to use micro or nano-liter volume of fluid, and are particularly studying on manipulating and pumping different types of fluid of minute volume either sequentially or simultaneously. Many kinds of micro-pumps and micro-valves have been developed to ensure the precision and controllability of such a microfluidic process.

SUMMARY OF THE INVENTION

In order to reduce the cost and size of the microfluidic biochips, the present invention provides a microfluidic cartridge with miniature biochip as the sensing device. In the cartridge, a solution reservoir also functions as a pumping chamber when driven by an external linear actuator. Combined with the microfluidic structures built in, the cartridge according to this invention is small in size, cheap to make, and easy to use. Additionally, it enables the user to handle and manipulate minute amount of solution and reagents to carry out the bio detection process precisely.

One aspect of the present invention is a microfluidic cartridge with solution reservoir-pump chamber comprising: a channel-chamber layer, a sealing layer for the channel-chamber layer, a printed circuit board bound with magnetoresistive biochip, and at least one fluid inlet, wherein:

the channel-chamber layer is provided with a waste reservoir, a reaction-detection chamber, at least one solution reservoir-pump chamber and at least one micro-channel wherein the waste reservoir has a waste outlet and communicates with the reaction-detection chamber via the micro-channel, and the other port of the reaction-detection chamber communicates with said solution reservoir-pump chamber and said fluid inlet via said micro-channel;

said solution reservoir-pump chamber includes a sample reservoir and a reagent reservoir with each consists of a cylindrical chamber and an elastic element used for sealing and pumping the liquid in said cylindrical chamber;

the sealing layer and the channel-chamber layer are aligned and sealed so as to completely form the waste reservoir, the reaction-detection chamber, the sealable solution inlet, the solution reservoir-pump chamber and the micro-channel;

a chip window is formed in a position of the sealing layer corresponding to the position of the reaction-detection chamber in said channel-chamber layer, wherein said chip window is aligned and sealed between said reaction-detection chamber and said magnetoresistive biochip on said printed circuit board to form a complete reaction-detection chamber with the surface of said magnetoresistive chip as the reaction and detection surface; and the surface of the magnetoresistive chip is bio-functionalized to form a biochip which is connected to a testing apparatus outside said microfluidic cartridge by a plurality of electrically conductive lines on the printed circuit board.

According to the present invention, said elastic element is an elastic spheroid or cylinder.

According to the present invention, said cylindrical chamber comprises a upper portion, a middle portion and a lower portion wherein said lower portion is in fluid connection with said micro-channel and wherein the diameter of the upper portion is larger than the diameter of the middle and lower portion and the diameter of the lower portion is equal to or bigger than that of the middle portion.

According to the present invention, one said cylindrical chamber has two elastic spheroids used for sealing and pumping the liquid in said cylindrical chamber. One of the two elastic spheroids is a larger spheroid which has a diameter slightly larger than the diameter of said upper portion of said cylindrical chamber, and the other one is a smaller spheroid which has a diameter slightly larger than the diameter of said middle portion but smaller than said lower portion of said cylindrical chamber; the liquid in said solution reservoir-pump chamber flows out through said lower portion when said smaller elastic spheroid is driven into said lower portion of said cylindrical chamber by said liquid which is pressured by said larger spheroid propelled by a external actuator.

Said elastic spheroid has a diameter slightly bigger than that of said cylindrical chamber, and, when driven by an actuator, said elastic spheroid pressures the liquid in said cylindrical chamber out and seals said cylindrical chamber fluid tightly.

According to the present invention, said printed circuit board bound with magnetoresistive biochip comprises printed circuit board, magnetoresistive biochip and conductive lines connecting said biochip to an external tester.

According to the present invention, the surface of said sealable solution inlet is sealed by a sealing material.

ADVANTAGES OF THE INVENTION

The present invention provides a microfluidic cartridge with solution reservoir-pump chamber for miniature magnetoresistive biochips. The solution reservoir-pump chamber integrates the solution reservoir and the pump chamber into a single object, significantly simplifying the cartridge's structure. With a precisely fabricated geometry, the volume of the solution stored in the reservoir can be accurately controlled. Driven by a computer-controlled actuator, the elastic spheroid in the reservoir acts as a pumping valve to inject solution into the reaction-detection chamber via micro-channels with a controlled flow rate. The sequence of injection of the different type of reagents or solution can be programmed into the computer controlling the linear actuator. With such an integrated yet simple solution reservoir-pimp chamber, the cartridge is easy to use and cheap to fabricate, making it a good option for disposable application.

REFERENCE SIGNS

Figure 1:
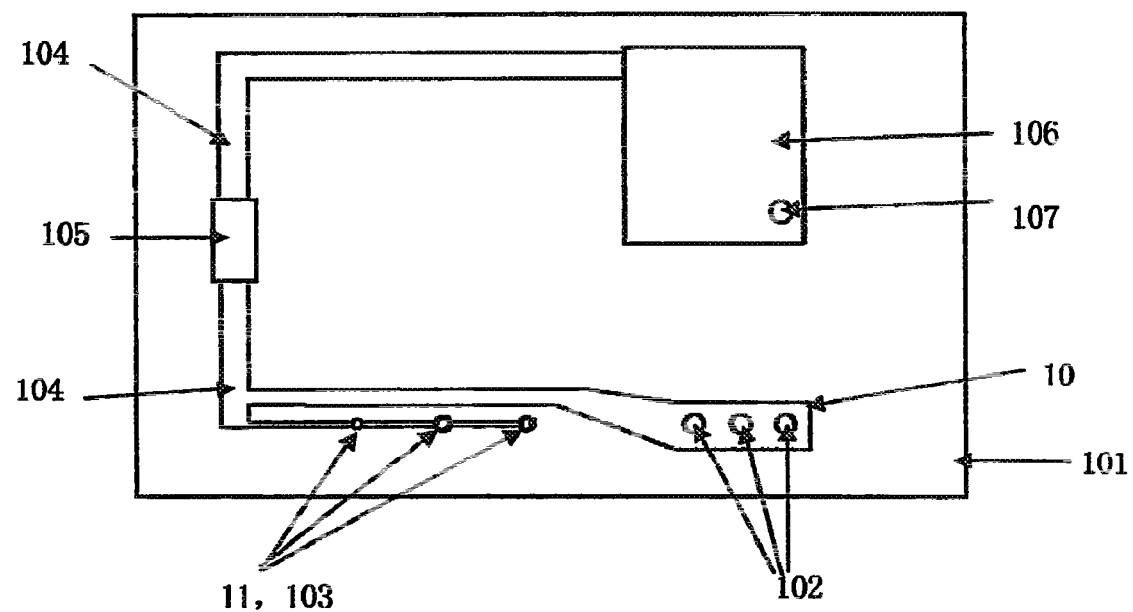
FIG. 1 shows the bottom surface of the channel-chamber layer of the microfluidic cartridge in the first embodiment, the surface to be sealed with the sealing layer.

10 The channel-chamber layer
11 The solution reservoir-pump chamber
12 The cylindrical chamber;
121, 122, 123 The upper, middle and lower portion of the cylindrical chamber, respectively
13 The elastic element;
131, 132 The elastic spheroids;
133, 134 The elastic cylinder
103 The inlets of the solution reservoir;
104 Micro-channels;
105 The reaction-detection chamber;
106 The waste reservoir;
107 waste outlet
20 The sealing layer for the channel-chamber layer;
21, 22 The upper and lower surface of the sealing layer, respectively;
201 The chip window;
203 The space for housing the bonding wires of the biochip;
30 The printed circuit board bound with biochip;
301 The magnetoresistive biochip;
302 The printed circuit board;
303 Electrical conductive lines
40 Solution injectors

DETAILED DESCRIPTION OF THE PREFERRED EMBODIMENT

Embodiment 1

Refer to FIGS. 1, 2A, 2B, 3, 4A, 4B, 5 and 6. The microfluidic cartridge comprises channel-chamber layer 10, seal layer for the channel-chamber layer 20, and printed circuit board 30.

The channel-chamber layer 10 shown in FIG. 1 includes substrate 101; sealable solution inlets 102; solution reservoir-pump chambers 11; partially constructed micro-channels 104; partially constructed reaction-detection chamber 105; partially constructed waste reservoir 106, and waste outlet 107. Said waste reservoir 106 is in fluidic connection with the reaction-detection chamber 105 via micro-channel 104. The other end of reaction-detection chamber 105 is communicated with solution reservoir-pump chambers 11 and solution inlets 102 via micro-channels 104.

Figure 2A:
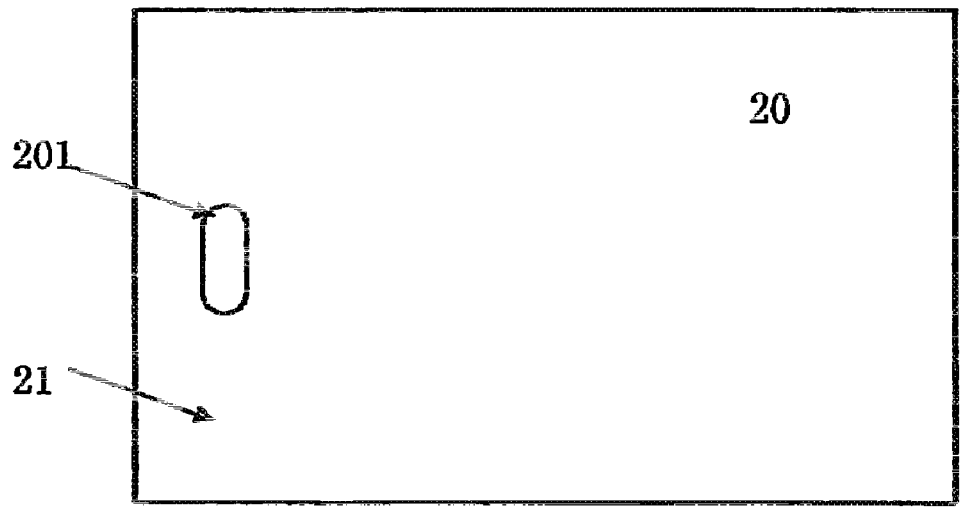
FIG. 2A shows the upper surface of the sealing layer, the surface to be sealed with the surface of the channel-chamber layer shown in FIG. 1.
Figure 2B:
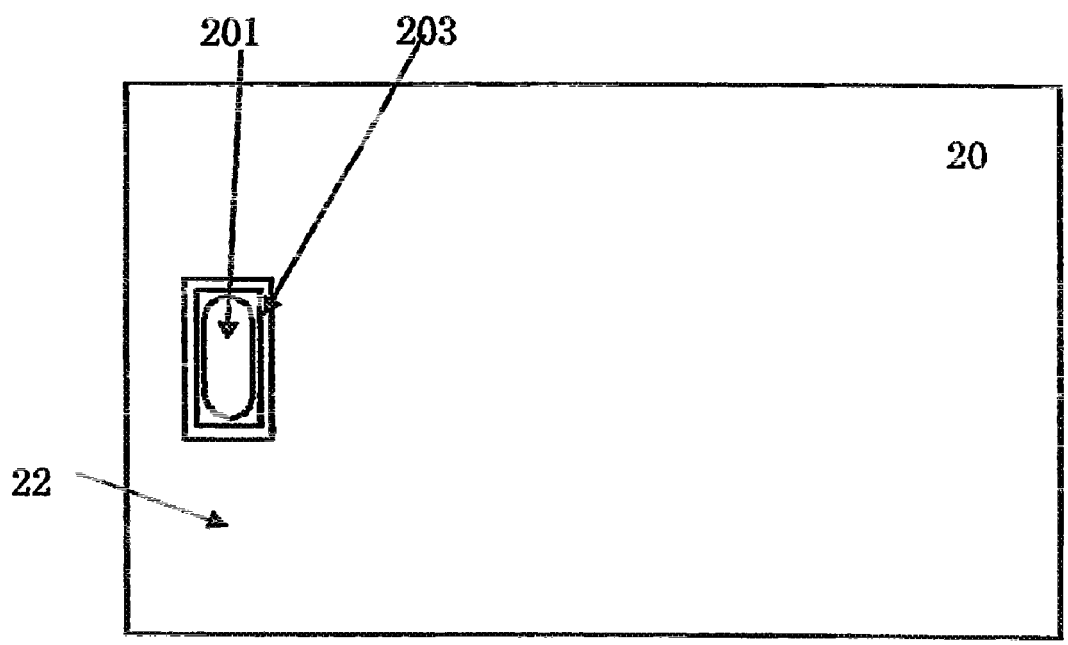
FIG. 2B shows the lower surface of the sealing layer, the surface to be sealed with the printed circuit board shown in FIG. 3.

Said sealing layer 20 shown in FIGS. 2A and 2B consists of an upper surface 21 and a lower surface 22. Chip window 201 on sealing layer 20 lines up with said reaction-detection chamber 105 in the channel and chamber layer 10 when sealed together. Upper surface 21 of sealing layer 20 is sealed to the surface, shown in FIG. 1, of said channel and chamber layer 10 to finish the construction of waste reservoir 106 and micro-channels 104. Yet reaction-detection chamber 105 is still not completed until the partially finished cartridge is sealed with printed circuit board 30.

Figure 3:
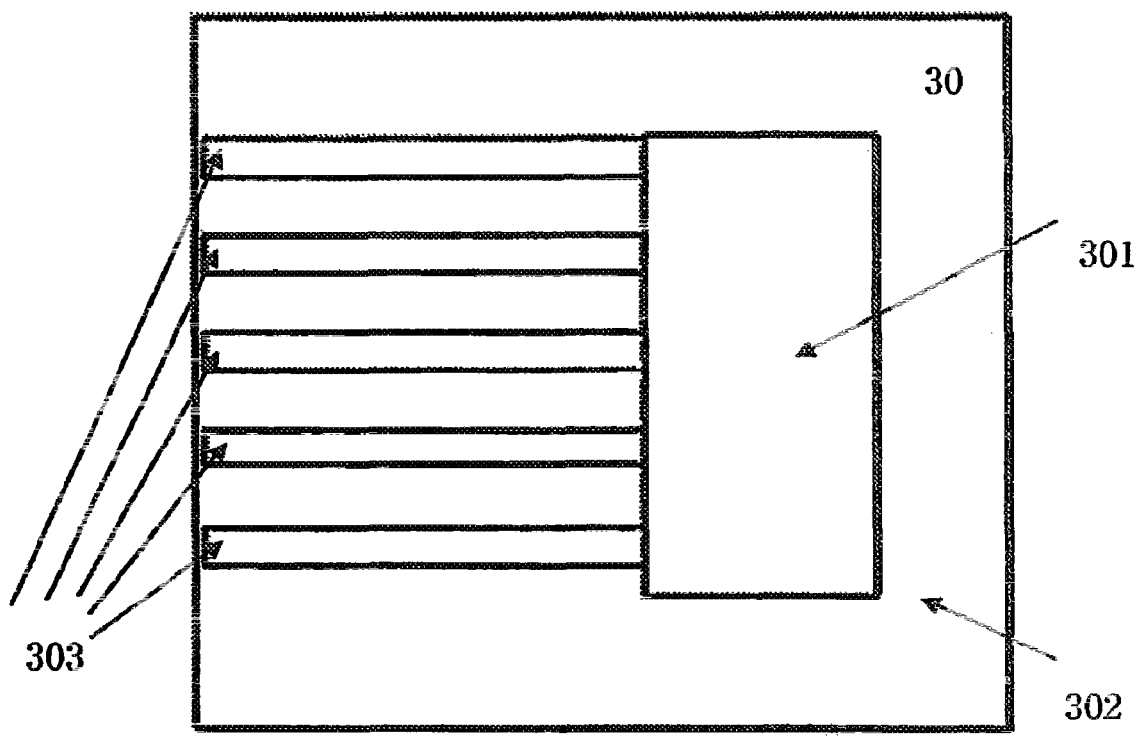
FIG. 3 shows the printed circuit board bound with magnetoresistive biochips in the first embodiment.

As shown in FIG. 2B, around the edge of chip window 201 of the sealing layer 20 is a recessed space for accommodating the bonding wires of biochip 301 on the printed circuit board 30 which is shown in FIG. 3. With printed circuit board 30 aligned and sealed fluid-tight with lower surface 22 of sealing layer 20, magnetoresistive biochip 301 fits into chip window 201 and functions as the reaction-detection surface of the complete cartridge on the bottom of reaction-detection chamber 105. As shown in FIG. 3, the printed circuit board 30 consists of printed circuit board 302, magnetoresistive biochip 301 and conductive lines 303.

Figure 4A:
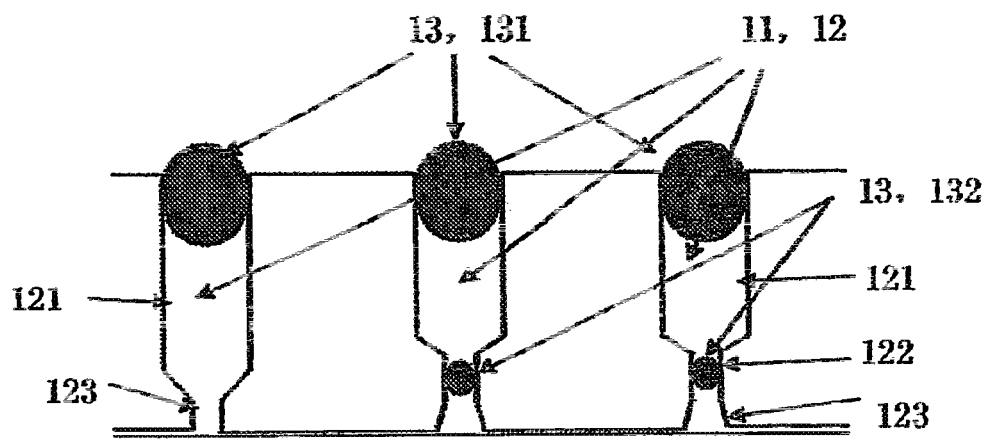
FIG. 4A shows the solution reservoir-pump chamber, with solution, in the first embodiment.
Figure 4B:
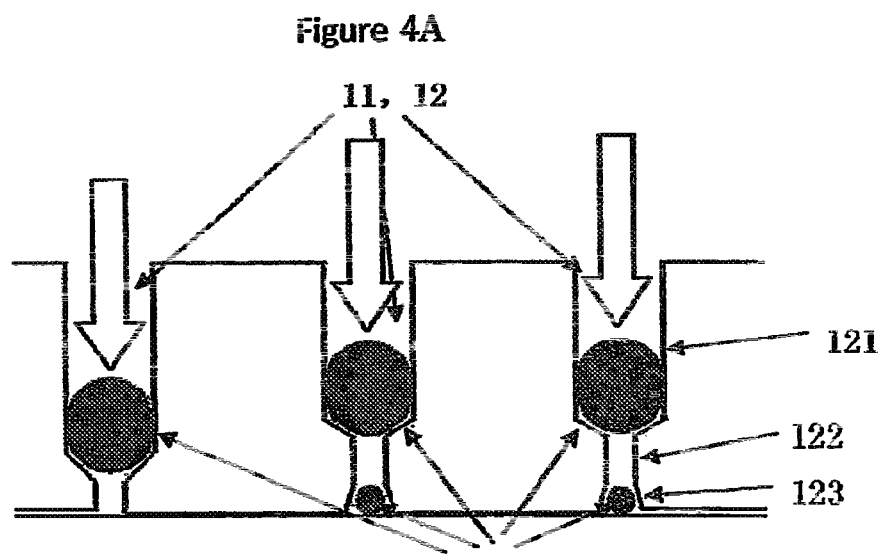
FIG. 4B shows the solution reservoir-pump chamber when solution is drained.

As shown in FIGS. 4A and 4B, solution reservoir-pump chamber 11 comprises cylindrical chamber 12 and elastic elements 13. Elastic elements 13 play both the role of sealing and pumping valve. Cylindrical chamber 12 can have two different structures: one with two butting cylindrical chambers of different diameters, and the other with three cylindrical chambers of different diameters. The diameter of upper portion 121 is bigger than the diameter of middle portion 122 and lower portion 123; the diameter of middle portion 122 is slightly smaller than that of lower portion 123. Elastic elements 13 have a diameter slightly bigger than those of the respective cylindrical chambers. More specifically, spheroids 131 have a diameter slightly bigger than the diameter of upper portion 121 of the cylindrical chamber and spheroids 132 have a diameter slightly bigger than the diameter of middle portion 122 but smaller than the diameter of lower portion 123. Spheroids 131 are first inserted into upper portion 121 to seal the top of chambers 11. Sample or solution is injected into chamber 11 via inlets 103 which are shown in FIG. 1. Spheroids 132 are then placed in middle portion 122 of chamber 11 to seal the chamber. When elastic spheroid 131 is driven towards the lower portion of the cylindrical chamber, solution pressures elastic spheroid 132 into portion 123 where the sealing effect of 132 disappears and flows out of the cylindrical chamber and into reaction-detection chamber 105 via micro-channels 104.

Figure 5:
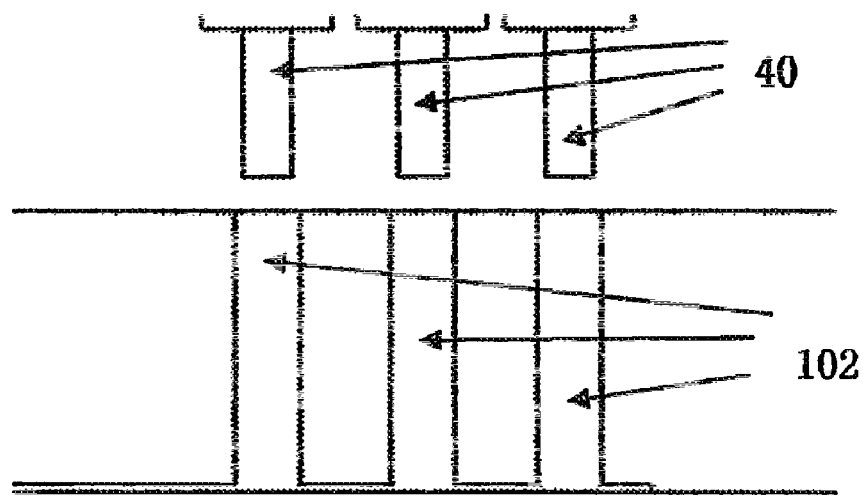
FIG. 5 shows the solution inlets in the first embodiment.

Solution inlets 102, shown in FIG. 5, are for injecting buffer solution or any reagents which are not stored in the solution reservoir-pump chamber. The inlets are sealed when not used. When in use, syringe needles 40 (external devices) pierce the sealing layer on top of inlets 102 to inject solution into reaction-detection chamber 105 via micro-channels 104.

Figure 6:
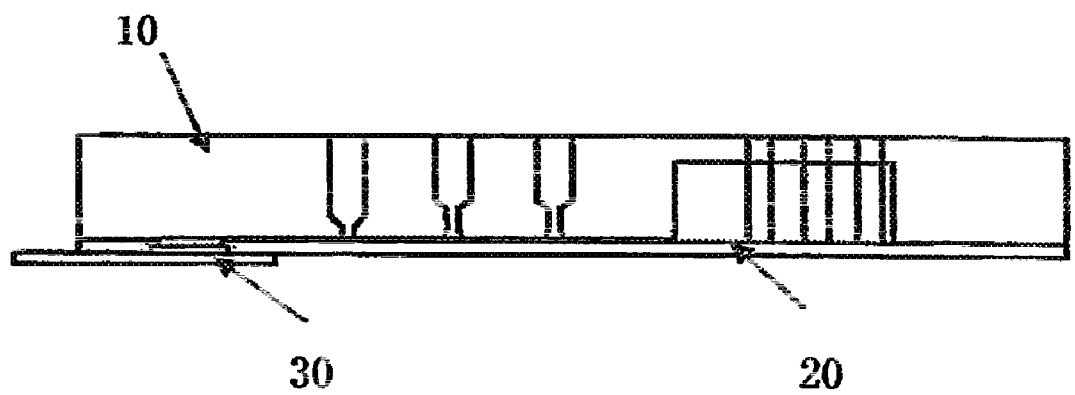
FIG. 6 is a side view of the assembled microfluidic cartridge in the first embodiment.

FIG. 6 is the side view of an assembled cartridge. In application, sample and reagents are added into at least one of the solution reservoirs, which is then sealed by an elastic element. The cartridge is placed into a testing apparatus. A linear actuator controlled by a programmable driver pushes the elastic spheroid downwards and squeezes solution out of the solution reservoir-pumping chamber and into the reaction-detection chamber via micro-channels. Sequentially or simultaneously, syringe needles controlled by programmable actuators move down and insert into the sealed inlets to inject solution. The inlets are sealed again when the syringe needles are drawn back.

Embodiment 2

Figure 4C:
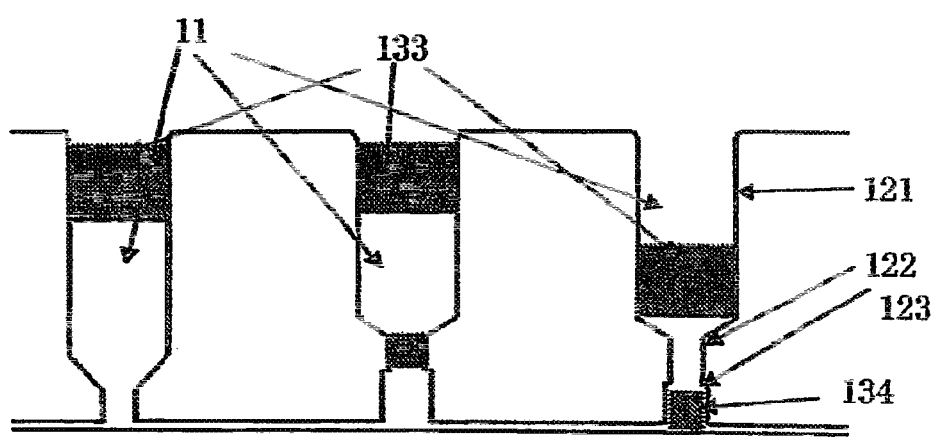
FIG. 4C shows the solution reservoir-pump chamber, with solution, in the second embodiment.

Refer to FIG. 4C. In comparison with embodiment 1, embodiment 2 has a structurally different solution reservoir-pump chamber 11, with elastic cylinders 133 and 134 being used for sealing and pumping solutions. Solution reservoir-pump chamber 11 comprises cylindrical chambers and elastic cylinders 133 and 134. Elastic cylinders 133 play both the roles of sealing and pumping valve, while 134 are only for sealing. Cylindrical chamber 11 can have two different structures: one with two butting cylindrical chambers of different diameters, and the other with three cylindrical chambers of different diameters. The diameter of upper portion 121 is bigger than the diameter of middle portion 122 and lower portion 123; the diameter of middle portion 122 is slightly smaller than that of lower portion 123. Cylinders 133 have a diameter slightly bigger than the diameter of upper portion 121 of the cylindrical chamber and cylinders 134 have a diameter slightly bigger than the diameter of middle portion 122 but smaller than the diameter of lower portion 123. Cylinders 133 are first inserted into upper portion 121 to seal the top of chamber 11. Sample or solution is injected into chamber 11 via inlets 103 which are shown in FIG. 1. Cylinders 134 are then placed in middle portion 122 of chamber 11 to seal the chamber. When elastic cylinders 133 is driven towards the lower portion of the cylindrical chamber, solution pressures elastic cylinders 134 into portion 123 where the sealing effect of 134 disappears and flows out of the cylindrical chamber and into reaction-detection chamber 105 via micro-channels 104.

Embodiment 3

Figure 7:
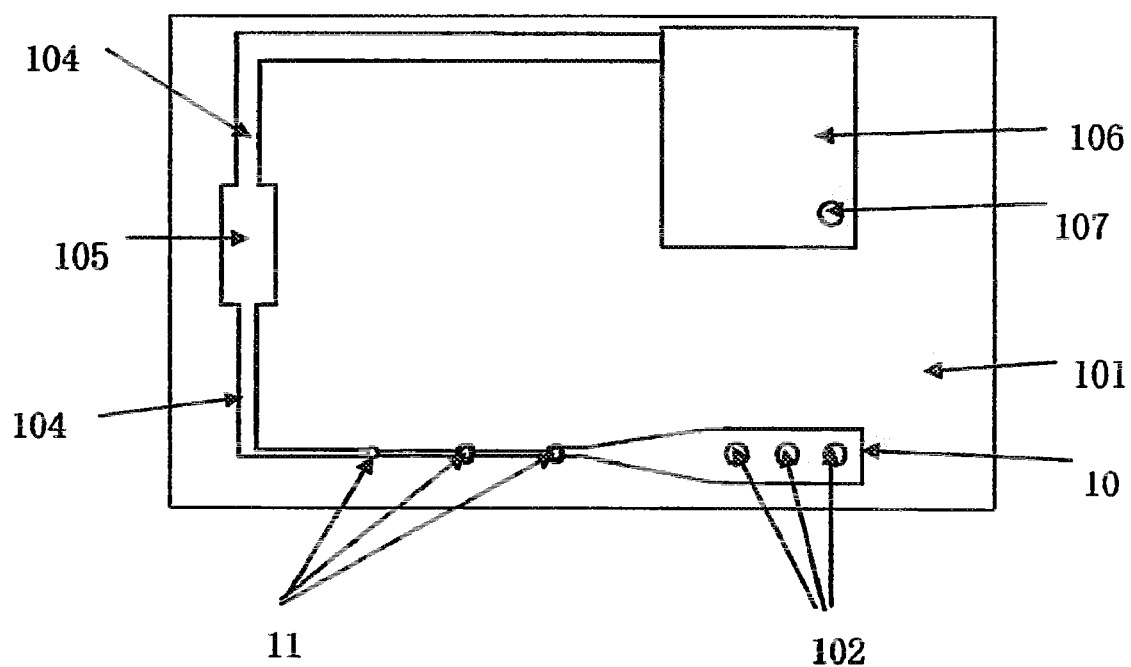
FIG. 7 is the lower surface of the microfluidic cartridge in the third embodiment.

Refer to FIG. 7.

In comparison with embodiment 1, the solution reservoir-pump chamber 11 of the channel-chamber layer 10 in embodiment 3 is located over the same micro-channel as solution inlets 102. Same as in embodiment 1, the microfluidic cartridge in embodiment 3 comprises a channel and chamber layer 10 shown in FIG. 7, a sealing layer 20 shown in FIG. 2A and 2B, and a printed circuit board 30 with magnetoresistive biochip and conductive lines shown in FIG. 3. The channel-chamber layer 10 consists of substrate 101, solution inlets 102, solution reservoir-pump chamber 11, partially constructed micro-channels 104, partially constructed reaction-detection chamber 105, and partially constructed waste reservoir 106 with waste outlet 107. Waste reservoir 106 is in fluid connection to the exit end of reaction-detection chamber 105 via micro-channel 104, and the other end of reaction-detection chamber 105 is in fluid connection to solution reservoir-pump chambers 11 which are in fluid connection with solution inlets 102. The structure of solution reservoir-pump chambers 11 can be either like the one shown in FIG. 4A which was described in detail in embodiment 1, or the one in FIG. 4C which was described in detail in embodiment 2, and are not described again. Similarly, the sealing layer and the printed circuit board were described in detail in embodiment 1, and are not repeated here.

The aforementioned embodiments show the details of the many aspects of the present invention. However, many modifications and variations of the embodiments can be made without departing from the spirit and scope of the present invention, as will be apparent to those skilled in the art. The specific embodiments described herein are offered by way of example only, and the invention is to be limited only by the terms of the appended claims, along with the full scope of equivalents to which such claims are entitled.

What is claimed is:

1. A microfluidic cartridge with solution reservoir-pump chamber comprising: a channel-chamber layer, a sealing layer for the channel-chamber layer, a printed circuit board bound with magnetoresistive biochip, and at least one sealable solution inlet, characterized in that:

the channel-chamber layer is provided with a waste reservoir, a reaction-detection chamber, at least one solution reservoir-pump chamber and at least one micro-channel wherein the waste reservoir has a waste outlet and communicates with the reaction-detection chamber via the micro-channel, and the other port of the reaction-detection chamber communicates with said solution reservoir-pump chamber and said sealable solution inlet via said micro-channel;

said solution reservoir-pump chamber includes a sample reservoir and a reagent reservoir with each consists of a cylindrical chamber and an elastic element used for sealing and pumping the liquid in said cylindrical chamber, wherein said elastic element is an elastic spheroid or cylinder;

the sealing layer and the channel-chamber layer are aligned and sealed so as to completely form the waste reservoir, the reaction-detection chamber, the sealable solution inlet, the solution reservoir-pump chamber and the micro-channel;

a chip window is formed in a position of the sealing layer corresponding to the position of the reaction-detection chamber in said channel-chamber layer, wherein said chip window is aligned and sealed between said reaction-detection chamber and said magnetoresistive biochip on said printed circuit board to form a complete reaction-detection chamber with the surface of said magnetoresistive chip as the reaction and detection surface; and the surface of the magnetoresistive chip is bio-functionalized to form a biochip which is connected to a testing apparatus outside said microfluidic cartridge by a plurality of electrically conductive lines on the printed circuit board.

2. The microfluidic cartridge in claim 1, wherein said cylindrical chamber comprises a upper portion, a middle portion and a lower portion wherein said lower portion is in fluid connection with said micro-channel and wherein the diameter of the upper portion is larger than the diameter of the middle and lower portion and the diameter of the lower portion is equal to or bigger than that of the middle portion.

3. The microfluidic cartridge in claim 1, wherein one said cylindrical chamber has two elastic spheroids used for sealing and pumping the liquid in said cylindrical chamber.

4. The microfluidic cartridge in claim 3, wherein one of the two elastic spheroids is a larger spheroid which has a diameter slightly larger than the diameter of said upper portion of said cylindrical chamber, and the other one is a smaller spheroid which has a diameter slightly larger than the diameter of said middle portion but smaller than said lower portion of said cylindrical chamber; the liquid in said solution reservoir-pump chamber flows out through said lower portion when said smaller elastic spheroid is driven into said lower portion of said cylindrical chamber by said liquid which is pressured by said larger spheroid propelled by a external actuator.

5. The microfluidic cartridge in claim 1, wherein said elastic spheroid has a diameter slightly bigger than that of said cylindrical chamber, and, when driven by an actuator, said elastic spheroid pressures the liquid in said cylindrical chamber out and seals said cylindrical chamber fluid tightly.

6. The microfluidic cartridge in claim 1, wherein said printed circuit board bound with magnetoresistive biochip comprises printed circuit board, magnetoresistive biochip and conductive lines connecting said biochip to an external tester.

7. The microfluidic cartridge in claim 1, wherein the surface of said sealable solution inlet is sealed by a sealing material.

* * * * *